US008183382B2

(12) United States Patent  (10) Patent No.: US 8,183,382 B2
Kadyrov et al.  (45) Date of Patent: May 22, 2012

(54) SULPHUR-CONTAINING METATHESIS CATALYSTS

(75) Inventors: Renat Kadyrov, Frankfurt (DE); Anna Szadkowska, Warsaw (PL); Karol Grela, Warsaw (PL); Michal Barbasiewicz, Erlangen (DE)

(73) Assignee: Evonik Degussa GmbH, Essen (DE)

( * ) Notice: Subject to any disclaimer, the term of this patent is extended or adjusted under 35 U.S.C. 154(b) by 647 days.

(21) Appl. No.: 12/109,092

(22) Filed: Apr. 24, 2008

(65) Prior Publication Data

US 2008/0275247 A1 Nov. 6, 2008

(30) Foreign Application Priority Data

May 3, 2007 (DE) .......................... 10 2007 020 694

(51) Int. Cl.
C07F 15/00 (2006.01)
(52) U.S. Cl. ........................................ 548/103; 556/136
(58) Field of Classification Search .................. 548/103; 556/136
See application file for complete search history.

(56) References Cited

U.S. PATENT DOCUMENTS

2002/0107138 A1  8/2002  Hoveyda

FOREIGN PATENT DOCUMENTS

| CN | 2005-100803792 | 7/2005 |
| DE | 198 15 275 A1 | 10/1999 |
| DE | 199 02 439 A1 | 8/2000 |
| EP | 118 0 108 | 2/2002 |
| JP | 2004506755 | 3/2004 |
| WO | 99-00397 A1 | 1/1999 |
| WO | 99-51344 A1 | 10/1999 |
| WO | 0214376 A2 | 2/2002 |
| WO | 2005003843 A1 | 6/2005 |
| WO | 2005-094345 A2 | 10/2005 |

OTHER PUBLICATIONS

Ben Asuly et al. "A Thermally Switchable Latent Ruthenium Olefin Metathesis Catalyst" Organometallics, Feb. 6, 2008, vol. 27, pp. 811-813.*
Chinese Office Action in CN 200810095607.7. Mailed Dec. 7, 2010 and English translation.
Hejl, et al. (2006) "Latent Olefin Metathesis Catalysts Featuring Chelating Alkylidenes" Organometallics. 25, 6149-6154.
Hejl, Andrew et al.: "Latent Olefin Metathesis Catalysts Featuring Chelating Alkylidenes" Organometallics, 25(26), 6149-6154 CODEN, 2006.
European Search Report received in EP08103339, mailed Oct. 27, 2008.
European Search Report received in JP2008-118437. Mailed Feb. 17, 2011.

* cited by examiner

*Primary Examiner* — Joseph Kosack
(74) *Attorney, Agent, or Firm* — Smith, Gambrell & Russell, LLP

(57) ABSTRACT

The present invention relates to novel transition metal complexes of the formula (I)

to a process for preparing these transition metal complexes and to the use of the transition metal complexes as catalysts in metathesis reactions.

4 Claims, 1 Drawing Sheet

SULPHUR-CONTAINING METATHESIS CATALYSTS

INTRODUCTION AND BACKGROUND

The present invention relates to novel transition metal complexes of the formula (I)

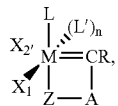

to a process for preparing these transition metal complexes and to the use of the transition metal complexes as catalysts in metathesis reactions.

Metathesis is understood to mean a chemical reaction in which formal substituents on double or triple bonds are exchanged. The metathesis reactions include the oligomerization and polymerization of acyclic dienes (ADMET) or polymerization of cyclic olefins (ROMP), and also the synthesis of cyclic compounds of different sizes by ring-closing metathesis (RCM). In addition, crossed metatheses of different alkenes (CM) and metathesis of alkenes with alkynes (ene-yne metathesis) are known. Numerous fundamental studies have contributed significantly to the understanding of this transition metal-catalysed reaction (for an overview see: Handbook of Metathesis, Ed. R. H. Grubbs, WILEY-VCH, Weinheim, 2003).

For olefin metathesis, a multitude of catalyst systems is available. Especially studies by Schrock introduced alkylidene complexes of molybdenum and of tungsten as the first well-defined catalysts (J. S. Murdzek, R. R. Schrock, Organometallics, 1987, 6, 1373-1374). However, a disadvantage was found to be the high sensitivity of these complexes. In recent times, ruthenium-alkylidene complexes with phosphine ligands have become established (P. Schwab et al. Angew. Chem. Int. Ed. Engl. 1995, 34, 2039-2041; P. A. van der Schaaf et al. J. Organometallic Chem. 2000, 606, 65-74). These complexes possess a high tolerance toward polar functional groups and are air- and water-stable. The introduction of N-heterocyclic carbenes (NHC) as ligands allowed not only the activity of these systems to be enhanced further, but also, owing to the significant variability of the ligand sphere, made available new kinds of control means for the reactions (DE 19815275 and T. Weskamp, W. C. Schattenmann, M. Spiegler, W. A. Herrmann Angew. Chem. 1998, 110, 263-2633). A further significant increase in the catalytic activity is achieved by supplementation with a more coordinatively labile ligand (DE 19902439 and T. Weskamp, F. J. Kohl, W. Hieringer, D. Gleich, W. A. Herrmann Angew. Chem., 1999, 111, 2573-2576).

Representative examples are the complexes A and B.

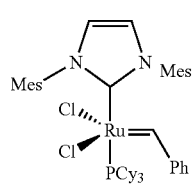

A

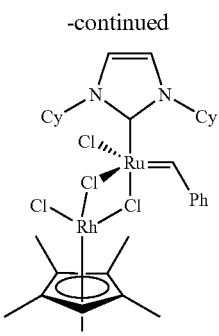

B

Gessler et al. (Tetrahedron Lett. 2000, 41, 9973-9976) and Garber et al. (J. Am. Chem. Soc. 2000, 122, 8168-8179) describe ruthenium complexes which, as well as an N-heterocyclic carbene ligand, have an isopropoxybenzylidene ligand. These so-called "green" catalysts have a higher stability and can optionally be recycled.

The patent WO 9900397 describes catalysts C and D, which are particularly suitable for ROMP. The further examples of such highly active metathesis catalysts (E and F) are described in the application WO 2005094345.

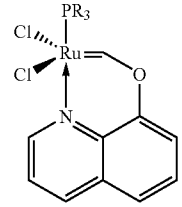

C

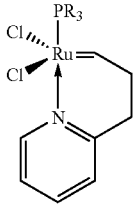

D

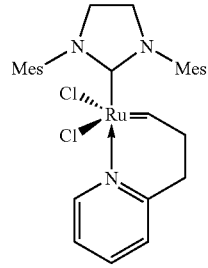

E

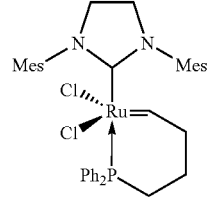

F

Some examples of metathesis catalysts with sulphur-containing units in the side chain have been described in the literature (complex H in P. A. van der Schaaf et al. J. Organometallic Chem. 2000, 606, 65-74, complex J1 in Patent CN 2005100803792 and complex J2 in M. Bieniek et al. J. Organomet. Chem. 2006, 691, 5289).

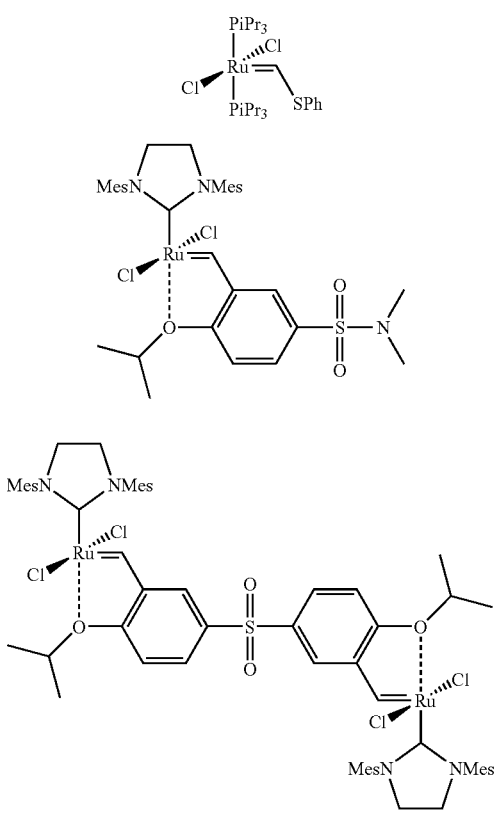

Nevertheless, there was still a need for novel catalyst systems for olefin metathesis which are stable and additionally exhibit a high, possibly controllable activity and can be utilized as alternative catalysts to the existing catalysts. In particular, the catalysts, viewed as a whole, should be superior to the prior art catalysts viewed from the economic and/or ecological standpoint.

SUMMARY OF INVENTION

Surprisingly, compounds of the formula (I) have now been found

(I)

in which
M is Ru or, Os, preferably Ru,
L and L' are the same or different and are each independently an uncharged electron donor,
X1 and X2 are the same or different and are each an anionic ligand,
R is hydrogen, a cyclic, straight-chain or branched-chain alkyl radical or optionally substituted aryl radical,
Z is a sulphur-containing unit which coordinates directly to the metal, and
A is a bridge which bonds the Z unit covalently to the carbene carbon, and n is 0 or 1, preferably 0.

Olefin metathesis with the inventive complexes is notable for low activity at room temperature and an especially rapid rise in activity with increasing temperature. As a result, the inventive compounds can be used as thermally switchable catalysts. Furthermore, the inventive complexes are air-stable compounds and have remarkable thermal stability with an activity which is not significantly lower than that of the prior art catalysts.

Variation of the uncharged electron donor ligands L and L' allows the activity and selectivity of the complexes also to be controlled as appropriate. The inventive complexes preferably have saturated or unsaturated NHC (N-heterocyclic carbenes) as ligands for L. As well as their variety for the modelling of the ligand sphere, these are notable especially for provision of high catalyst activities. Such ligands are mentioned by way of example in the following literature: DE 19815275 and T. Weskamp, W. C. Schattenmann, M. Spiegler, W. A. Herrmann Angew. Chem. 1998, 110, 263-2633; DE 19902439 and T. Weskamp, F. J. Kohl, W. Hieringer, D. Gleich, W. A. Herrmann Angew. Chem., 1999, 111, 2573-2576; EP 1180108. L' may be L or assume the structures listed in WO 9951344 as uncharged electron donor ligands.

In the inventive complexes, the abovementioned sulphur-containing Z unit is preferably radicals from the group of: thiol, thioether, thioacetals, disulphides, dithiocarboxylic acids, thioesters, thioketones, thioaldehydes, thiocarbamates, thiourethanes, phosphine sulphides, thiophosphates, thiophosphonates, sulphonates, sulphones, sulphonamides or sulphur-containing heterocycles, while it must be ensured that the compound Z-M, preferably Z—Ru, is formed via the sulphur atom or an oxygen atom disposed on the sulphur. This will preferably be the case when the coordinating ring closure between the sulphur or the oxygen atom and the metal atom forms a 5-, 6- or 7-membered ring.

For the bridging molecular moiety A, the person skilled in the art can in principle use a radical which appears to be useful for the present purpose: preference is given to a carbon skeleton which consists of 2 to 4 carbon atoms, particular preference to a $C_2$ bridge, where the two carbon atoms may have $sp^2$ hybridization and the radical advantageously forms part of a 3-, 4-, 5-, 6-, 7- or 8-membered ring system. The ring systems just addressed may optionally have one or more heteroatoms. Useful such heteroatoms are especially oxygen, sulphur or nitrogen atoms. They may be unsaturated further over and above the $sp^2$ hybridization described and optionally be of aromatic nature. They may be mono- or polysubstituted by further radicals, especially those selected from the group consisting of $(C_1-C_8)$-alkyl, $(C_1-C_8)$-alkoxy, $(C_6-C_{18})$-aryloxy, HO—$(C_1-C_8)$-alkyl, $(C_2-C_8)$-alkoxyalkyl, $(C_6-C_{18})$-aryl, $(C_7-C_{19})$-aralkyl, $(C_3-C_{18})$-heteroaryl, $(C_4-C_{19})$-heteroaralkyl, $(C_1-C_8)$-alkyl-$(C_6-C_{18})$-aryl, $(C_1-C_8)$-alkyl-$(C_3-C_{18})$-heteroaryl, $(C_3-C_8)$-cycloalkyl, $(C_1-C_8)$-alkyl-$(C_3-C_8)$-cycloalkyl, $(C_3-C_8)$-cycloalkyl-$(C_1-C_8)$-alkyl.

In addition, the ring systems may also have one or more substituents, especially those selected from the group consisting of halogen, hydroxyl, carboxylic acids, esters, silyl ethers, thioethers, thioacetals, imines, silyl enol ethers, ammonium salts, amides, nitriles, perfluoroalkyl groups, ketones, aldehydes, carbamates, carbonates, urethanes, sulphonates, sulphones, sulphonamides, nitro groups, organosilane units, phosphonate and phosphate groups, and phosphonium salts.

In the inventive complexes, the anionic ligands X1 and X2 are preferably inorganic or organic anions from the group of halides, especially $F^-$, $Cl^-$, $Br^-$, pseudohalides, hydroxides, alkoxides or amides (RO⁻, R₂N⁻), phenols, thiols, thiophenols, carboxylates, carbonates, sulphonates, sulphates, phosphates and phosphonates, allyl and cyclopentadienyl, the pseudohalides being understood to mean preferably cyanide, thiocyanate, cyanate, isocyanate and isothiocyanate, where the R radicals satisfy the definition given below.

Very particular preference is given to complexes of the general formula (II) and (III).

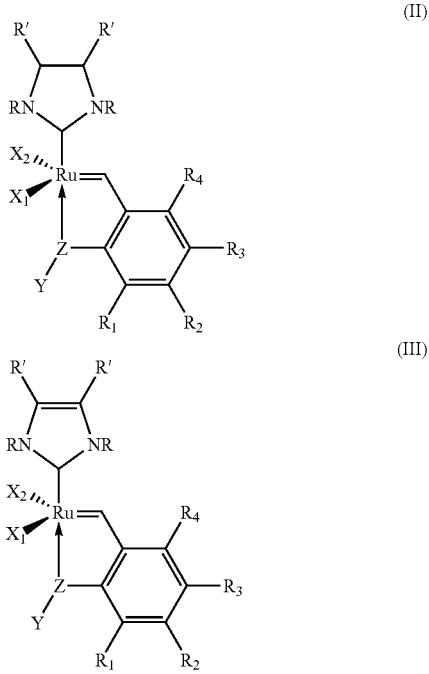

In these complexes, Z is —S—, —S(O)— and S(O)₂—, $X_1$ and $X_2$ assume the definitions given above, Y, R, R' and $R_1$ to $R_4$ are each independently selectable radicals from the group of hydrogen, ($C_1$-$C_8$)-alkyl, ($C_1$-$C_8$)-alkoxy, ($C_6$-$C_{18}$)-aryloxy, HO—($C_1$-$C_8$)-alkyl, ($C_2$-$C_8$)-alkoxyalkyl, ($C_6$-$C_{18}$)-aryl, ($C_7$-$C_{19}$)-aralkyl, ($C_3$-$C_{18}$)-heteroaryl, ($C_4$-$C_{19}$)-heteroaralkyl, ($C_1$-$C_8$)-alkyl-($C_6$-$C_{18}$)-aryl, ($C_1$-$C_8$)-alkyl-($C_3$-$C_{18}$)-heteroaryl, ($C_3$-$C_8$)-cycloalkyl, ($C_1$-$C_8$)-alkyl-($C_3$-$C_8$)-cycloalkyl, ($C_3$-$C_8$)-cycloalkyl-($C_1$-$C_8$)-alkyl. Moreover, the R' and $R_1$ to $R_4$ radicals may each independently be: (cyclo)alkylthio, (hetero)arylthio, alkyl/arylsulphonyl, alkyl/arylsulphynyl, in each case optionally substituted by ($C_1$-$C_8$)-alkyl, ($C_1$-$C_8$)-alkoxy, ($C_6$-$C_{18}$)-aryloxy, HO—($C_1$-$C_8$)-alkyl, ($C_2$-$C_8$)-alkoxyalkyl, ($C_6$-$C_{18}$)-aryl, perfluoroalkyl, halogen, ($C_1$-$C_8$)-acyloxy, ($C_1$-$C_8$)-acyl ($C_1$-$C_8$)-alkoxycarbonyl, ($C_1$-$C_8$)-alkylsulphonyl or ($C_1$-$C_8$)-alkylsulphinyl, ($C_6$-$C_{18}$)-arylsulphonyl or ($C_6$-$C_{18}$)-arylsulphinyl.

$R_1$ to $R_4$ may likewise be a nitro group, sulphate, amine, ammonium salt, phosphate and phosphonium salt.

The R' radicals may be present with one or more of the $R_1$ to $R_4$ radicals bonded to one another in cyclic compounds. The $R_1$ radical may also be joined to the Y radical to form a (hetero)cyclic compound.

The inventive compounds, especially those of the formula (I) and (II), are preferably prepared by exchange reaction of the phosphine ligand in compounds of the formula (IV) for ligands of the formula (V)

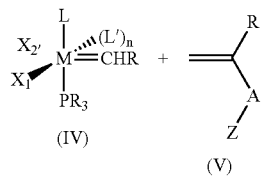

in which the radicals each assume the definitions specified above and $PR_3$ is a phosphine ligand, preferably tricyclohexylphosphine.

The inventive compounds, especially those of the formula (I) and (II) are prepared from compounds of the formula (VI) preferably in a solvent, more preferably in toluene, benzene, tetrahydrofuran or dichloromethane, most preferably in dichloromethane. The reaction preferably takes place in the presence of compounds which are capable of scavenging phosphines, more preferably in the presence of $CuCl_2$ and CuCl, most preferably in the presence of CuCl. Preference is given to working in the presence of equimolar amounts or of an excess of phosphine scavenger, based on compounds of the formula (IV). When the phosphine scavenger used is CuCl, particular preference is given to using 1 to 1.5 equivalents. Preference is given to using 0.9 to 3 equivalents of the compounds of the formula (V), based on compounds of the formula (IV), particular preference to using 1 to 2 equivalents. The reaction is effected preferably at temperatures of 20 to 80° C., more preferably at temperatures of 30 to 50° C. The reaction is preferably carried out under inert gas, for example nitrogen or argon.

The inventive compounds (I), especially those of the formula (II) and (III), can be used as catalysts in metathesis reactions. They can be used, for example, in ring-closing metatheses. They are more preferably used in ROMP and ADMET polymerization reactions.

Alkyl radicals are considered especially to be ($C_1$-$C_8$)-alkyl radicals, for example methyl, ethyl, n-propyl, isopropyl, n-butyl, isobutyl, sec-butyl, tert-butyl, pentyl, hexyl, heptyl or octyl including all of their bonding isomers.

The ($C_1$-$C_8$)-alkoxy radical corresponds to the ($C_1$-$C_8$)-alkyl radical with the proviso that it is bonded to the molecule via an oxygen atom.

($C_2$-$C_8$)-Alkoxyalkyl means radicals in which the alky chain is interrupted by at least one oxygen function, but two oxygen atoms cannot be bonded to one another. The number of carbon atoms indicates the total number of carbon atoms present in the radical.

A ($C_3$-$C_5$)-alkylene bridge is a carbon chain with three to five carbon atoms, this chain being bonded to the molecule in question via two different carbon atoms.

The radicals described in the preceding paragraphs may be mono- or polysubstituted by halogens and/or radicals containing nitrogen, oxygen, phosphorus, sulphur, silicon atoms. These are especially alkyl radicals of the type mentioned above which have one or more of these heteroatoms in their chain or which are bonded to the molecule via one of these heteroatoms.

($C_3$-$C_8$)-Cycloalkyl is understood to mean cyclopropyl, cyclobutyl, cyclopentyl, cyclohexyl or cycloheptyl radicals, etc. They may be substituted by one or more halogens and/or radicals containing nitrogen, oxygen, phosphorus, sulphur, silicon atoms and/or have nitrogen, oxygen, phosphorus, sulphur atoms in the ring, for example 1-, 2-, 3-, 4-piperidyl, 1-, 2-, 3-pyrrolidinyl, 2-, 3-tetrahydrofuryl, 2-, 3-, 4-morpholinyl.

A $(C_3-C_8)$-cycloalkyl-$(C_1-C_8)$-alkyl radical denotes a cycloalkyl radical as represented above, which is bonded to the molecule via an alkyl radical as specified above.

In the context of the invention, $(C_1-C_8)$-acyloxy means an alkyl radical as defined above with max. 8 carbon atoms, which is bonded to the molecule via a COO function.

In the context of the invention, $(C_1-C_8)$-acyl means an alkyl radical as defined above with max. 8 carbon atoms, which is bonded to the molecule via a CO function.

An aryl radical is understood to mean especially a $(C_6-C_{18})$-aryl radical which is an aromatic radical having 6 to 18 carbon atoms. In particular, this includes compounds such as phenyl, naphthyl, anthryl, phenanthryl, biphenyl radicals or systems of the type described above fused to the molecule in question, for example indenyl systems, which may optionally be substituted by halogen, $(C_1-C_8)$-alkyl, $(C_1-C_8)$-alkoxy, $NH_2$, $NH(C_1-C_8)$-alkyl, $N((C_1-C_8)$-alkyl$)_2$, OH, $CF_3$, $NH(C_1-C_8)$-acyl, $N((C_1-C_8)$-acyl$)_2$, $(C_1-C_8)$-acyl, $(C_1-C_8)$-acyloxy.

A $(C_7-C_{19})$-aralkyl radical is a $(C_6-C_{18})$-aryl radical bonded to the molecule via a $(C_1-C_8)$-alkyl radical.

In the context of the invention, a $(C_3-C_{18})$-heteroaryl radical denotes a five-, six- or seven-membered aromatic ring system which is composed of 3 to 18 carbon atoms and has heteroatoms, for example nitrogen, oxygen or sulphur, in the ring. Such heteroaromatics are considered especially to be radicals such as 1-, 2-, 3-furyl, 1-, 2-, 3-pyrrolyl, 1-, 2-, 3-thienyl, 2-, 3-, 4-pyridyl, 2-, 3-, 4-, 5-, 6-, 7-indolyl, 3-, 4-, 5-pyrazolyl, 2-, 4-, 5-imidazolyl, acridinyl, quinolinyl, phenanthridinyl, 2-, 4-, 5-, 6-pyrimidinyl. This radical may be substituted by the same radicals as the aryl radical specified above.

A $(C_4-C_{19})$-heteroaralkyl is understood to mean a heteroaromatic system corresponding to the $(C_7-C_{19})$-aralkyl radical.

Useful halogens (Hal) include fluorine, chlorine, bromine and iodine.

DETAILED EMBODIMENTS OF INVENTION

Examples

1. Synthesis of 2-(isopropylthio)benzoic acid

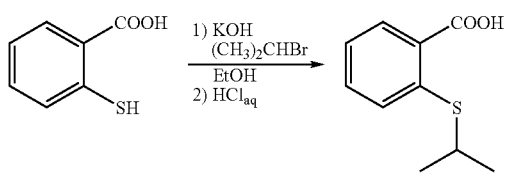

Figure 1:
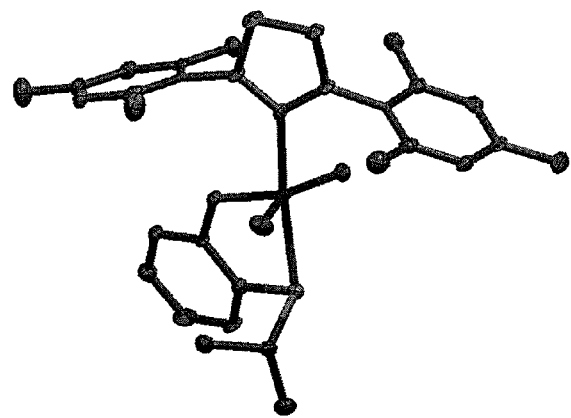
FIG. 1 shows a Crystal structure of complex SR1.

To a suspension of thiosalicylic acid (16.7 g; 109 mmol; Fluka) and isopropyl bromide (20.0 g; 163 mmol) in ethanol (125 ml) were added slowly, with vigorous stirring, KOH pellets (17.3 g; 433 mmol). After stirring for 6 h, the reaction mixture was poured into water-ice mixture (1200 ml) and acidified with concentrated hydrochloric acid (approx. 50 ml). The precipitated product was filtered off, washed with 50% aqueous ethanol (2×100 ml) and dried under reduced pressure. Yield 6.4 g (30%).

IR (film): v 3084, 3058, 2962, 2924, 2865, 1828, 1625, 1588, 1463, 1365, 1243, 1197, 1155, 1049, 991, 912, 769, 746 cm$^{-1}$; $^1$H NMR (200 MHz, DMSO-$d_6$) δ 1.74-1.82 (d, 6H, J=2.2 Hz), 4.02-4.12 (septet, 1H, J=6.6 Hz), 7.70 (m, 1H), 7.66-7.72 (m, 1H), 7.95-8.00 (m, 2H), 8.36-8.42 (m, 1H); $^{13}$C NMR (50 MHz, DMSO-$d_6$) δ 22.4, 35.3, 124.6, 128.3, 131.1, 132.1, 140.3, 167.2, 205.6; MS (EI) m/z (rel intensity) 196 (21, [M]$^+$), 154(13), 137(11), 136(100), 108(21), 69(8), 43(13), 41(13), 39(12); HRMS (EI): calcd for [M]$^+$ ($C_7H_{12}O_2S$): 196.05580. found 196.05604.

2. Synthesis of 2-(isopropylthio)benzaldehyde

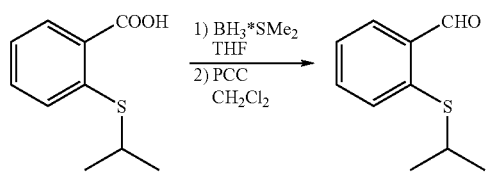

To a solution of 2-(isopropylthio)benzoic acid (0.98 g, 5 mmol) in THF (10 ml) was added dropwise borane-dimethyl sulphide complex (0.8 ml, 8 mmol) at 3° C. under argon with vigorous stirring. After continuing to stir in an ice bath for 30 min, the reaction was left to stand at RT for a further 24 h. Methanol (1.5 ml) was added cautiously and the reaction solution was concentrated under reduced pressure. The residue was taken up in diethyl ether (50 ml), and washed with saturated $K_2CO_3$ solution and NaCl solution. Aqueous solutions were additionally extracted with ether, the combined organic phases were dried over $MgSO_4$ and filtered, and the solvent was removed under reduced pressure. The residue was taken up in dichloromethane (30 ml), admixed cautiously with PCC (1.20 g, 5.6 mmol) and stirred at room temperature for 36 h. After solvent removal, the residue was purified by column chromatography on silica gel (10:1 hexane:ethyl acetate). Yield 0.69 g (76%).

IR (film): v 3686, 3601, 3362, 3063, 2968, 2929, 2867, 2744, 1950, 1692, 1648, 1587, 1559, 1460, 1442, 1383, 1368, 1287, 1242, 1195, 1156, 1128, 1073, 1062, 1052, 1039, 931, 879, 845, 825, 777, 679, 660, 635, 509 cm-1; 1H NMR (200 MHz, CDCl3) δ 1.30-1.40 (d, 6H, J=6.6 Hz), 3.38-3.48 (septet, 1H, J=6.8 Hz), 7.25-7.60 (m, 3H), 7.84-7.92 (m, 1H), 10.54 (d, 1H, J=0.63 Hz); 13C NMR (50 MHz, CDCl3) δ 22.9, 38.8, 126.7, 130.1, 132.4, 133.8, 135.8, 140.3, 191.9; MS (EI) m/z (rel intensity) 180(66, [M]+.), 165(18), 138(49), 137(100), 110(35), 109(41), 104(57), 69(11), 66(11), 65(26), 43(25), 41(19), 39(17); HRMS (EI): calcd for [M]+. (C, 10; H, 12; O, S): 180.07122. found 180.07148.

3. Synthesis of 2-isopropylsulphinylbenzaldehyde

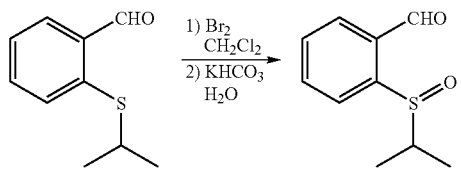

A solution of 2-(isopropylthio)benzaldehyde (0.33 g, 1.83 mmol) in dichloromethane (10 ml) was admixed with aqueous $KHCO_3$ solution (1.18 g in 10 ml of $H_2O$). With vigorous stirring, a solution of bromine (0.310 g, 1.93 mmol) in dichloromethane (1.5 ml) was added dropwise. After continuing to stir for 20 min, a spatula-tip of $Na_2SO_3$ was added, and the organic phase was removed, washed with saturated NaCl solution, dried over $MgSO_4$ and filtered, and the solvent was removed under reduced pressure. The residue was purified by column chromatography on silica gel (3:1 to 1:1 hexane:ethyl acetate). The product precipitated out as a yellowish oil. Yield 0.304 g (85%).

IR (film): v 3447, 2963, 2917, 2864, 2738, 1702, 1628, 1607, 1482, 1439, 1380, 1264, 1227, 1183, 1158, 1121, 1105, 1037, 992, 950, 932, 852, 803, 751, 697, 635, 593, 578, 535, 506, 446, 418 cm-1; 1H NMR (200 MHz, CDCl3) δ 0.86-0.94 (d, 3H, J=6.8 Hz), 1.50-1.56 (d, 3H, J=7.1 Hz), 2.90-3.10 (septet, 1H, J=6.8 Hz), 7.60-8.00 (m, 1H), 8.16-8.22 (m, 1H), 10.01-10.06 (d, 1H J=0.63 Hz); 13C NMR (50 MHz, CDCl3) δ 21.7, 38.2, 124.4, 130.5, 133.9, 135.2, 144.9, 198.5; MS (EI) m/z (rel intensity) 180(66, [M]+.), 165(18), 138(49), 137(100), 110(35), 109(41), 104(57), 69(11), 66(11), 65(26), 43(25), 41(19), 39(17); HRMS (EI): calcd for [M]+. (C, 7; H, 10; O, 2; S): 178.08162. found 178.08148.

4. Wittig Olefination

To a suspension of methyltriphenylphosphonium bromide (0.690 g, 1.93 mmol, Aldrich) in 8 ml of THF was added dropwise n-BuLi (1.5 M, 1.4 ml, 2.07 mmol) at −78° C. under an argon atmosphere. The yellow reaction solution was warmed to room temperature within 1 h. After cooling again to −78° C., a solution of the appropriate aldehyde (1.39 mmol) in THF (5 ml) was added, then the mixture was warmed slowly to room temperature and stirred at this temperature for 1 h. After adding a saturated $NH_4Cl$ solution, the aqueous phase was extracted with ethyl acetate (4×20 ml). The combined organic phases were dried over $MgSO_4$ and the solvent was removed under reduced pressure. The residue was purified by column chromatography on silica gel (2:8 cyclohexane:ethyl acetate).

4a. 2-Isopropylthio-1-vinylbenzene

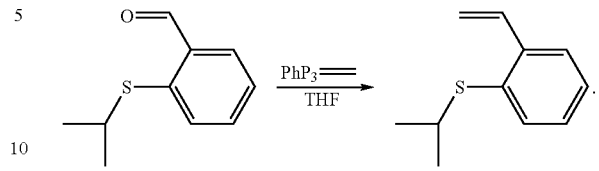

Yield 74%.

IR (film): v 3084, 3058, 2962, 2924, 2865, 1828, 1625, 1588, 1463, 1365, 1243, 1197, 1155, 1049, 991, 912, 769, 746 cm$^{-1}$; 1H NMR (500 MHz, CDCl3) δ 1.26 (d, 6H, J=6.7 Hz), 3.24-3.33 (septet, 1H, J=6.7 Hz), 5.30 (dd, 1H, J=1.2, 11 Hz), 5.67 (dd, 1H, J=1.2, 17.5 Hz), 7.18-7.27 (m, 2H), 7.35 (dd, 1H, J=11, 17.5 Hz), 7.42-7.47 (m, 1H), 7.52-7.57 (m, 1H); 13C NMR (125 MHz, CD3CCD3) δ 23.1, 38.8, 115.3, 125.9, 127.5, 127.9, 133.8, 133.9, 135.3, 140.2; MS (EI) mlz (rel intensity) 178 (9, [M]+.), 136(10), 135(100), 134(14), 91(18), 77(2), 65(1), 43(2); HRMS (EI): calcd for [M]+.($C_{11}H_{14}S$): 178.08162. found 178.08148.

4b. 2-Isopropylsulphinyl-1-vinylbenzene

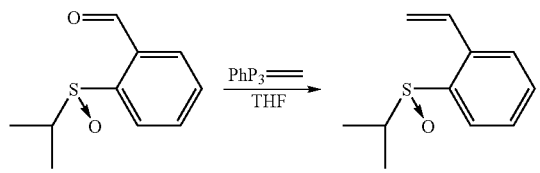

Yield 71%.

IR (film): v 3686, 3603, 3411, 2982, 2933, 2870, 2543, 2049, 1969, 1940, 1856, 1727, 1628, 1606, 1562, 1465, 1440, 1414, 1384, 1366, 1193, 1158, 1125, 1069, 1024, 990, 956, 926, 891, 875, 638, 582, 549, 506 cm$^{-1}$; 1H NMR (400 MHz, CDCl3) δ 1.06 (d, 3H, J=7.0 Hz), 1.3 (d, 3H, J=7.0 Hz), 2.83-2.93 (septet, 1H, J=7.1 Hz), 5.41 (dd, 1H, J=0.83, 11 Hz), 5.77 (dd, 1H, J=0.96, 17.3 Hz), 6.93-7.02 (q, 1H, J=11 Hz), 7.44-7.58 (m, 2H), 7.86-7.89 (m, 1H, J=11, 17.5 Hz); 13C NMR (100 MHz, CDCl3) δ 13.1, 17.1, 53.2, 117.8, 124.8, 125.7, 128.3, 130.7, 131.6, 135.9, 139.8; MS (EI) m/z (rel intensity) 194 (4, [M]+.), 152(13), 137(10), 136(11), 135 (100), 134(11), 91(21), 77(11), 51(7), 45(8), 43(11), 41(9), 39(8); HRMS (EI): calcd for [M]+.($C_{11}H_{14}OS$): 194. 07654. found 194.07703.

5. Ru Complex Synthesis

To a suspension of copper(I) chloride (13 mg, 0.12 mmol) and tricyclohexylphosphine[1,3-bis(2,4,6-trimethylphenyl)-4,5-dihydroimidazol-2-ylidene][benzylidene]ruthenium(IV) dichloride (102 mg; 0.12 mmol) in 2 ml of dichloromethane was added a solution of the appropriate styrene derivative (0.132 mmol) dissolved in 3 ml of dichloromethane. After stirring at 40° C. for 20 min, the reaction solution was concentrated under reduced pressure. The residue was taken up in 20 ml of ethyl acetate and filtered through a Pasteur pipette with silica gel. The filtrate was concentrated again under reduced pressure and the residue was washed with a very small amount of ethyl acetate and cold pentane.

5a. Complex SR1

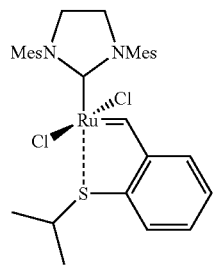

Green microcrystalline solid, yield 86%.

IR (film): v 2952, 2908, 2862, 1606, 1479, 1420, 1382, 1262, 1154, 1055, 1033, 863, 843, 798, 742 cm$^{-1}$; $^1$H NMR (500 MHz, CDCl$_3$) δ 0.99 (d, 6H, J=6.6 Hz), 2.37 (s, 6H), 2.48 (s, 12H), 3.18 (septet, 1H, J=6.6 Hz), 4.14 (s, 4H), 6.73 (d, 1H, J=7.5 Hz), 7.03 (s, 4H), 7.11-7.20 (m, 1H); 7.40-7.52 (m, 2H), 17.33 (s, 1H); $^{13}$C NMR (125 MHz, CD$_3$COCD$_3$) δ 19.5, 21.0, 51.7, 121.8, 123.3, 129.3, 129.4, 133.6, 136.4, 138.1, 138.6, 140.0, 140.3, 156.2, 162.0, 210.0, 285.7;

MS (EI) m/z (rel intensity) 642 (8, [M]$^{+\cdot}$), 530(10), 528 (18), 527(14), 526(13), 525(10), 305(40), 304(100), 303(91), 289(19), 287(10), 166(25), 163(12), 159(12), 158(22), 149 (19), 146(12), 145(14), 144(13), 135(14), 124(32), 91(45), 77(15), 71(11), 57(14), 55(12), 45(10), 44(46), 43(33), 42(12), 41(35), 40(31), 39(20), 38(15), 36(46); HRMS (EI): calcd for [M]$^{+\cdot}$ (C$_{31}$H$_{38}$N$_2$$^{35}$Cl$_2$S $^{102}$Ru): 642. 11762. found 642.11634.

FIG. 1: Crystal structure of complex SR1.

5b. Complex SOR1

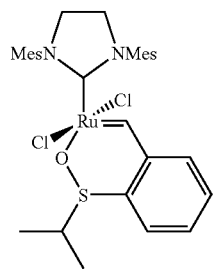

Light green microcrystalline solid, yield 72%:

IR (film): v 3447, 2963, 2917, 2738, 1702, 1628, 1607, 1482, 1439, 1380, 1264, 1227, 1183, 1158, 1121, 1105, 1037, 992, 950, 932, 852, 803, 751, 697, 635, 593, 578, 535, 506, 446, 418 cm$^{-1}$; $^1$HNMR (500 MHz, CDCl$_3$) δ 1.05 (q, 6H, J=6.7 Hz), 2.29 (m, 3H), 2.35-2.45 (m, 12H), 2.55 (s, 3H), 3.61 (septet, 1H, J=6.7 Hz), 4.15 (s, 4H), 6.74 (d, 1H, J=7.6 Hz), 6.95-7.05 (m, 4H), 7.34 (m, 1H), 7.65 (m, 1H) 7.72-7.78 (m, 1H), 16.81 s, 1H); $^{13}$C NMR (125 MHz, CDCl$_3$) δ 21.0, 51.7, 121.0, 127.5, 128.9, 129.4, 129.6, 129.7, 133.9, 135.4, 138.1, 138.5, 138.9, 139.0, 156.2, 207.2, 301.3; MS (ESI; m/z): 658 [M−Cl+CH$_3$CN]$^+$.

6. RCM of N,N-diallyl-p-toluenesulphonamide

6a. In the Presence of Complex SR1

A solution of N,N-diallyl-p-toluenesulphonamide (0.350 mmol, 84 mg) in 17.5 ml of toluene was admixed with 5 mol % of catalyst (0.018 mmol) SR1 from Example 5a under argon, and stirred at 80° C. A 200 µl aliquot of the reaction solution was added to 500 µl of 2M ethyl vinyl ether solution in methylene chloride and analysed by means of GC. After 24 h, 51% conversion to the desired N-p-toluenesulphonyl-2,5-dihydropyrrole was found.

6b. In the Presence of Complex SOR1

A solution of N,N-diallyl-p-toluenesulphonamide (0.350 mmol, 84 mg) in 17.5 ml of dichloromethane was admixed with 5 mol % of catalyst (0.018 mmol) SOR1 from Example 5b under argon, and stirred at room temperature. A 200 µl aliquot of the reaction solution was added to 500 µl of 2M ethyl vinyl ether solution in methylene chloride and analysed by means of GC. The progress of the reaction is shown in FIG. 2.

Figure 2:
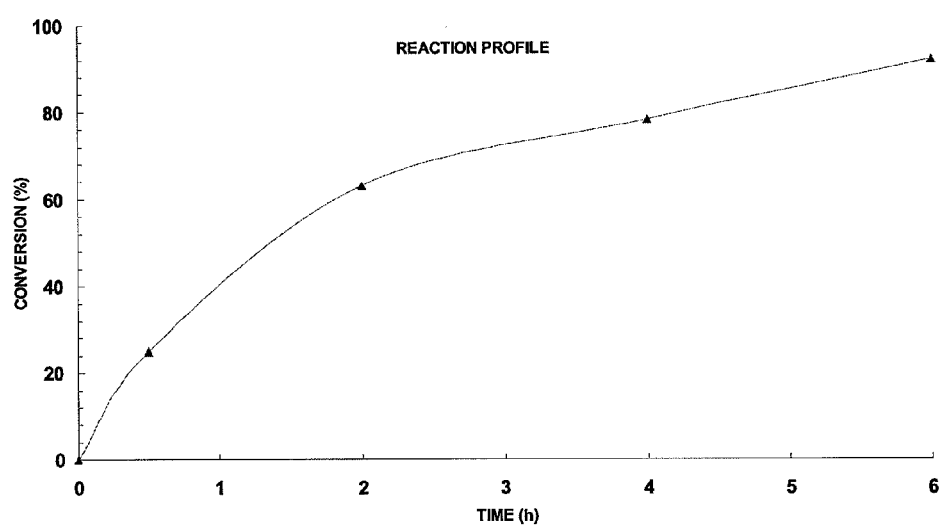
FIG. 2 is a graph of the percent conversion versus time.

FIG. 2: RCM of N,N-diallyl-p-toluenesulphonamide in the presence of 5 mol % of complex SOR1 in methylene chloride at room temperature.

7. RCM of diethyl 2-allyl-2-(2-methylallyl)malonate

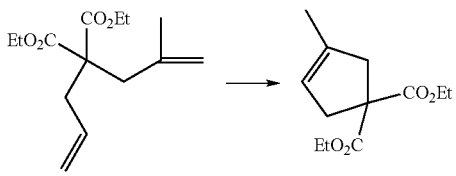

A solution of diethyl 2-allyl-2-(2-methylallyl)malonate (0.350 mmol) in 17.5 ml of toluene was admixed with 1 mol % of catalyst (0.0035 mmol) SOR1 from Example 5b under argon, and stirred at 80° C. 200 µl of the reaction solution were added to 500 µl of 2M ethyl vinyl ether solution in methylene chloride and analysed by means of GC. After 1 h, 99% conversion to the desired 4,4-bis(ethoxycarbonyl)-1-methylcyclopentene was found.

8. Ene-yne metathesis of 3-allyloxy-3,3-diphenylpropyne

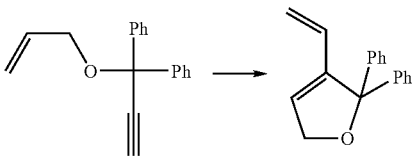

A solution of 3-allyloxy-3,3-diphenylpropyne (0.350 mmol) in 17.5 ml of toluene was admixed with 5 mol % of catalyst (0.018 mmol) SR1 from Example 5a under argon, and stirred at 80° C. 200 µl of the reaction solution were added to 500 µl of 2M ethyl vinyl ether solution in methylene chloride and analysed by means of GC. After 1 h, 99% conversion to the desired 3-ethenyl-2,5-dihydro-2,2-diphenylfuran was found.

We claim:

1. A compound of the formula (II) or (III)

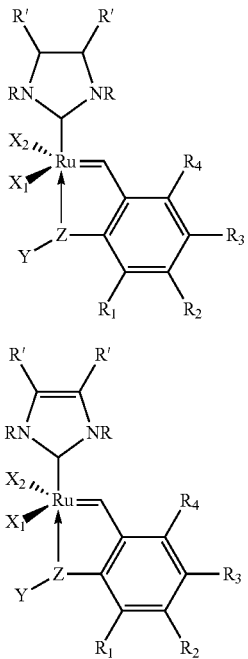

wherein Z is —S—, —S(O)— and S(O)$_2$—,

X1 and X2 are the same or different and are each an anionic ligand,

Y, R, R' and R$_1$ to R$_4$ are each independently selected from the group of hydrogen, (C$_1$-C$_8$)-alkyl, (C$_1$-C$_8$)-alkoxy, (C$_6$-C$_{18}$)-aryloxy, HO—(C$_1$-C$_8$)-alkyl, (C$_2$-C$_8$)-alkoxyalkyl, (C$_6$-C$_{18}$)-aryl, (C$_7$-C$_{19}$)-aralkyl, (C$_3$-C$_{18}$)-heteroaryl, (C$_4$-C$_{19}$)-heteroaralkyl, (C$_1$-C$_8$)-alkyl-(C$_6$-C$_{18}$)-aryl, (C$_1$-C$_8$)-alkyl-(C$_3$-C$_{18}$)-heteroaryl, (C$_3$-C$_8$)-cycloalkyl, (C$_1$-C$_8$)-alkyl-(C$_3$-C$_8$)-cycloalkyl, and (C$_3$-C$_8$)-cycloalkyl-(C$_1$-C$_8$)-alkyl.

2. The compound according to claim 1, wherein X1 and X2 are each inorganic or organic anion selected from the group consisting of a halide, a pseudohalide, hydroxide, an alkoxide, an amide, a phenol, a thiol, a thiophenol, a carboxylate, a carbonate, a sulphonate, a sulphate, a phosphate a phosphonate, allyl$^-$ and cyclopentadienyl$^-$, the pseudohalide being understood to mean a cyanide, a thiocyanate, a cyanate, an isocyanate and an isothiocyanate.

3. The compound according to claim 2, wherein the halide is F$^-$, Cl$^-$ or Br$^-$.

4. A process of metathesis comprising carrying out a metathesis reaction in the presence of a compound according to claim 1 as catalyst.

* * * * *